(12) United States Patent
Marley

(10) Patent No.: US 7,942,670 B2
(45) Date of Patent: May 17, 2011

(54) LOCKING SYSTEM FOR SCREWS FOR DENTAL IMPLANTS AND THE LIKE

(76) Inventor: William Jay Marley, Homer, AK (US)

( * ) Notice: Subject to any disclaimer, the term of this patent is extended or adjusted under 35 U.S.C. 154(b) by 185 days.

(21) Appl. No.: 12/380,719

(22) Filed: Mar. 2, 2009

(65) Prior Publication Data

US 2010/0221680 A1    Sep. 2, 2010

(51) Int. Cl.
*A61C 8/00* (2006.01)
(52) U.S. Cl. .......... 433/173; 433/172; 411/910
(58) Field of Classification Search .......... 433/172–176; 411/910
See application file for complete search history.

(56) References Cited

U.S. PATENT DOCUMENTS

| | | | | |
|---|---|---|---|---|
| 3,732,621 A | * | 5/1973 | Bostrom | 433/174 |
| 5,813,858 A | * | 9/1998 | Singer | 433/173 |
| 6,857,874 B2 | * | 2/2005 | Kim | 433/173 |

FOREIGN PATENT DOCUMENTS

| | | | |
|---|---|---|---|
| CH | 663145 AS | * | 11/1987 |
| DE | 19850097 A1 | * | 5/2000 |

* cited by examiner

*Primary Examiner* — John J Wilson
(74) *Attorney, Agent, or Firm* — Michael J. Tavella

(57) ABSTRACT

Disclosed is a means of locking the head of a screw to an abutting area. This is depicted in (FIG. 5) reference numeral (52) whereby the screw-head is locked in place to the abutting area (26) via filling void areas (56) and (32) with plasticized materials which then become solid. The voids are such that the head of the screw (52) cannot be located in any position in relation to the abutting area (26) but that some voids and some metal projections approximate each other, partial or complete. The locking material becomes a part of a seal to the septic area of the dental implant system (FIG. 6), (56) and (52). The septic area seal (FIG. 2) is completed with a small layer of sealing cement in that area between the abutment (26) distal end (44) and the proximal end of the implant body (24).

16 Claims, 4 Drawing Sheets

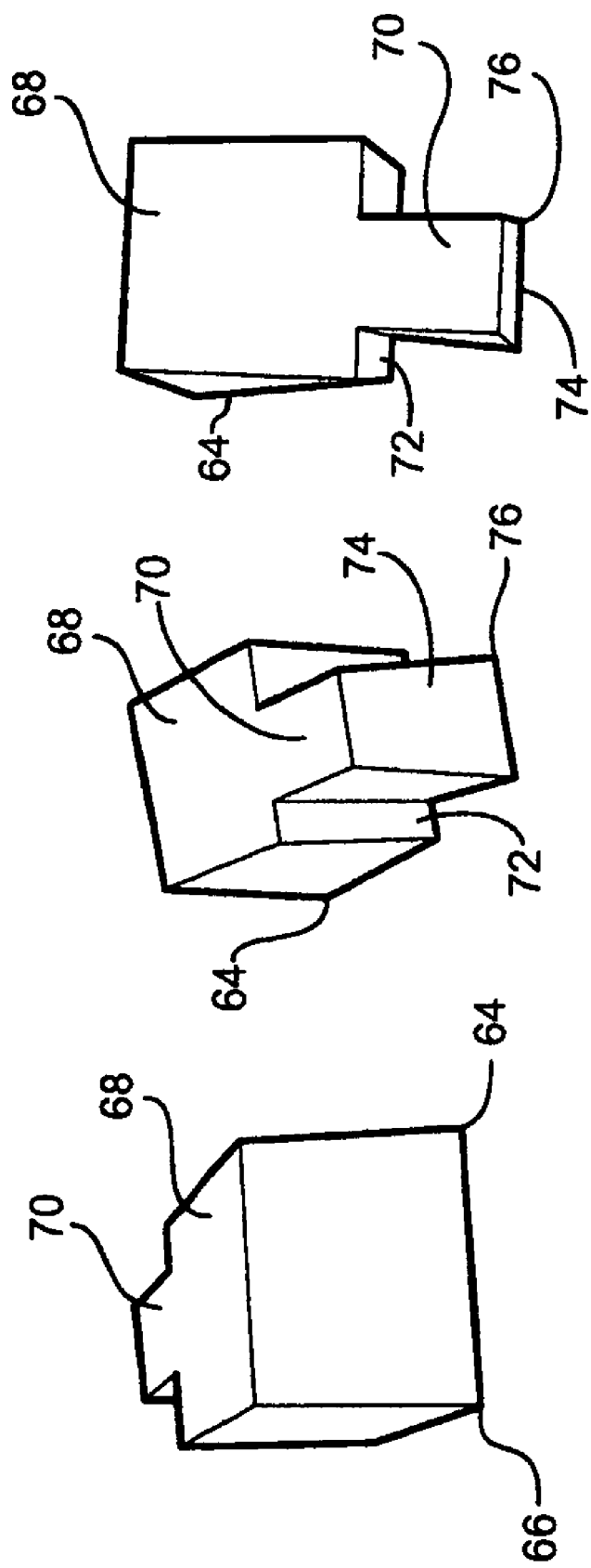

LOCKING SYSTEM FOR SCREWS FOR DENTAL IMPLANTS AND THE LIKE

CROSS-REFERENCE TO RELATED APPLICATIONS

Not applicable

FEDERALLY SPONSORED RESEARCH

Not applicable

BACKGROUND

Field of Invention

This invention relates to locking in place the head of a screw to an abutment; thus, securing the abutment to a dental implant body.

BACKGROUND

Tooth loss has lead to shortened life span, compromised quality of life via socially unacceptable appearance and the simple inability to masticate food as the first part of digestion. For the last several decades dental implants and dental prostheses (crowns) placed upon the implant system have become predictably successful and accepted from the aspects of medical biology, dental esthetics and masticating function.

Once the dental implant is placed and secure in the bone-receiving site a second structure has to be placed upon the dental implant body called the abutment. The abutment is held to the implant body by a screw. Screw loosening due to biting (occlusal) forces as well as frequent temperature changes of over 100 degrees F. from hot versus cold foods and liquids cause screw loosening to occur. Imperfections in the manufacture of dental implant systems also contribute to screw loosening. This has been reported to be as high as 65% over a three year period of time in past literature. (IMPLANT SCREW MECHANICS, Edwin A McGlumphy, DDS, Ms, Deborah A Mendel, DDS, and Julie A Holoway, DDS, Dental Clinics of North America Volume 42. Number 1. January 1998)

Screw loosening of the dental prosthesis can cause damage to the approximating and opposing dentition such as tooth loosening and fracturing. Loose screws themselves are much more likely to fracture and, if unable to retrieve the now fractured screw end, it may necessitate surgery to remove the useless dental implant body, and, if possible, surgically place a new implant body. Loose screws are cited as the cause of the submersion of dental implant bridges where at least one tooth abutment is a natural tooth and one or more abutments is a dental implant. The submersion of a natural tooth in this circumstance can necessitate extensive dental treatment to correct the damaged tooth and bridge. In addition, re-tightening a loosened screw requires, at a minimum, a visit to a dental practitioner and some means of gaining access to the implant abutment screw head. If the screw head is accessible through the prosthetic crown via an access filling (not shown) the screw can be tightened and a new replacement access filling placed as a consequence of a dental office visit. If, however, the abutment screw is not accessible via an access filling on top of the crown prosthesis (which has become more and more the common practice) the crown prosthesis then needs to be removed from the abutment which may necessitate damage or destruction of the prosthesis requiring as much as several patient visits to the dental practitioner to take impressions, make a temporary crown and replace the re-fabricated new crown prosthesis. In either case, the loosened screw is an expense to the patient in terms of time and money and an expense to the dental practitioner in terms of his or her time and the professional expense of not living up to a patient's expectations.

PRIOR ART

Prior patents have been made to address loosened screws but none have brought about a totally locked screw head.

Kim, U.S. Pat. No. 6,857,874 B2; Feb. 22, 2005, proposed using keyways that were inserted between the abutment and the screw head via axial slots in the screw head as well as complementary slots in the internal periphery of the abutment to secure the screw in place. This has several deficiencies. The screw must be tightened in such a manner as to require the axial slots of the screw and the abutment to be precisely aligned. This can be extremely difficult if not nearly impossible to the microscopic degree needed since the screw typically fits down inside the bore hole in the proximal portion of the abutment and has to be visualized, often in a dental mirror, upside down and backwards with the screw driving device in place and difficult lighting. Once the screw head is accessed and visualized it is practice to tighten the screw to a given manufacturer's torque specification. With U.S. Pat. No. 6,857,874 B2, Kim, in most cases, once the manufacturer's torque specification is achieved the screw head will need to be backed off, counter rotated, in the attempt to achieve the precise alignment of the slots of the screw and the slots of the abutment to be able to receive the very small keyways. Even once the slots are lined up to their (improbable) precise, exact configuration it would yet be extremely difficult to place the very small keyways in said slots. This complication is due to the inevitable very small size of the nearly microscopic keyways to be placed in a very small, confined, highly difficult region to visualize and access. These keyways also need to be manufactured at additional expense and effort.

This would be difficult in all the regions of the mouth but would be particularly difficult in the posterior molar regions. The small size of the keyways would also necessitate a greater than normal proximal distal axial height of the screw head to bring about the forces sought for the anti-rotational effect of the screw head. This screw head height could compromise future prosthetic crown considerations. Further, the keyways in slots configuration does not form any kind of an antiseptic seal between the screw and the abutment. Saliva and all its microbial components with no other provision can and will percolate in this septic area. This area is between the implant screw and the bore hole of the abutment and the bore hole of the implant body.

The septic space cited above is a warm, moist and dark area which has frequent opportunities to receive rich nutrients to allow microbial growth.

This area receives very little flushing from normal salivary flow and action. Microbial growth in these areas certainly can lead to unwanted microbial growth in the rest of the oral region and can add to halitosis (bad breath) as well.

Ines Aravena & Ajay Kumar, U.S. Pat. No. 6,986,660 B2, Jan. 17, 2006 depicts a spring loaded bilateral bearing that presses against the bore hole walls of the abutment. While this may provide a tighter fitting screw it nevertheless is not locked and should not be considered to be any tighter in its retentiveness than to the point at which it has been tightened (torqued). Once tightened the bearing must be in a given position related to the lateral walls of the bore-hole of the abutment wall which cannot be visualized nor detected. If the bearing is not engaged in the abutment detent it could cause serious compromise in the manufacturer's torque tightness recommendation and eventual screw retention. In addition, manufacturing the spring and ball bearings in the screw head would be difficult and also weaken the screw head and cause it to be much more vulnerable to fracture once it is applied as a screw. It also leaves a septic space as previously mentioned above. The spring holding the ball bearings in their lateral positions will lose some of its lateral force in time; thus, weakening the effect it has in pushing the ball bearings in a lateral direction. The assembly also requires the screw head area above the screw threads to be larger in a proximal distal aspect than is otherwise necessary causing, in certain circumstances, a compromised esthetic and functional, prosthetic result.

Ines Aravena and Ajay Kumar U.S. Pat. No. 7,300,283 B2 uses a spring washer with flexible legs that express themselves out in a lateral position and press into elongated channels, slots or grooves, created in the medial peripheral area of the abutment, much as is the case of the ball bearing proposed by the same Aravena and Kumar in U.S. Pat. No. 6,986,660 B2, Jan. 17, 2006. This, again, depends on a spring to hold the screw head in place and can be no tighter than was the screw head torqued to in the first place; thus, is not a true locking mechanism. In addition, in the construction of the channels, grooves or slots in the medial peripheral area of the abutment the lateral support of the screw head becomes compromised by a greatly reduced metal to metal contact area. The existence of the channels, grooves or slots creates unnecessary open septic spaces. There is no way to know if the spring legs have engaged the flat channels, grooves or slots once the final torqued position of the screw is obtained. The spring leg could well be resting on one of the ridges which would have to exist between the channels, slots or grooves in the abutment which, with minimal force, could cause the screw and spring to move. The spring with its legs is an additional device, which would have to be manufactured, and the springed legs could well lose their tension, in time, negating their effect.

Robert H. Milne U.S. Pat. No. 5,704,788, Jan. 6, 1998; Provides for a tab to lock a screw in position but takes occlusal (proximal distal) space and requires that the screw end up in an exact location to have the slots that the outer parts of the tab slide into. This is extremely difficult to do especially in the practice setting of highly compromised opportunity to visualize the tabs and the grooves with the driving instruments obstructing view in addition to often being viewed upside down and backwards in a dental mirror. Often, in a microscopic sense, this may not even be achievable or the tabs would have to be so ill fitting as to lose their locking effect. The description of the preferred embodiments even accounts for the fact that the screw may have to be loosened by 30 degrees from its tightened position to allow the tabs to slide into the slots since the tabs fitting in the slots dictate the final position of the tightened screw. The hex drive, with the tabs on it, must have room to slide down into the screw head and shank to allow the tabs to engage the slots. This has to weaken the already very small diameter screw shank and cause it to be subject to fracture in usage.

Bjorn Kvist U.S. Pat. No. 5,169,308, Dec. 8, 1992; Has a screw on top of the screw in an attempt to lock the first screw in place. This requires significant occlusal (proximal distal) height which in many cases compromises fabricating a prosthetic crown. The setscrew on top of the first screw only prevents the first screw from coming loose as long as it remains in its tightened position; thus, while it is preventative, it is not locking. It does not, at all, address sealing off the septic space. This process also requires the additional manufacturing of the screw and any drive that accompanies it.

SUMMARY

The invention to be described is very simple to manufacture and place, creates a true screw head-lock to abutment in any final position of the tightened screw. It can be executed by a dental practitioner with minimal time and effort with existing equipment and materials in any present day dental practice. Using a dental cement at the interface of the abutment & implant body will create a seal of said septic space. This invention has wide application in other service areas.

DRAWING FIGURES

Figure 4:
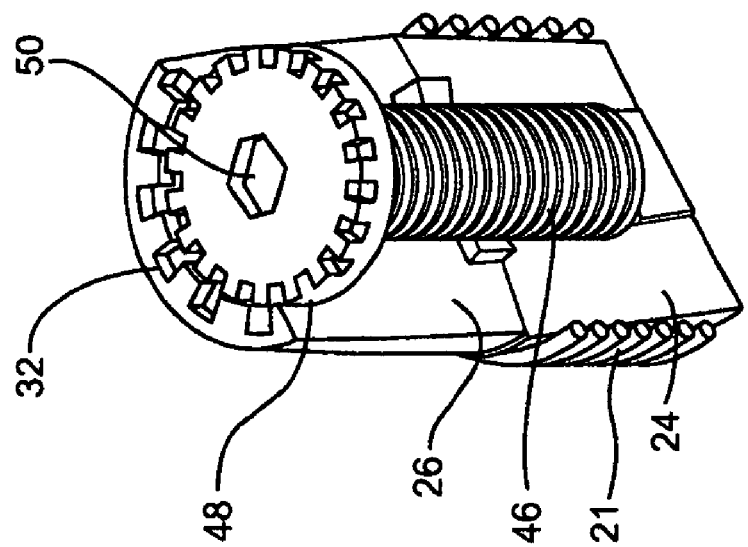
Figure 3:
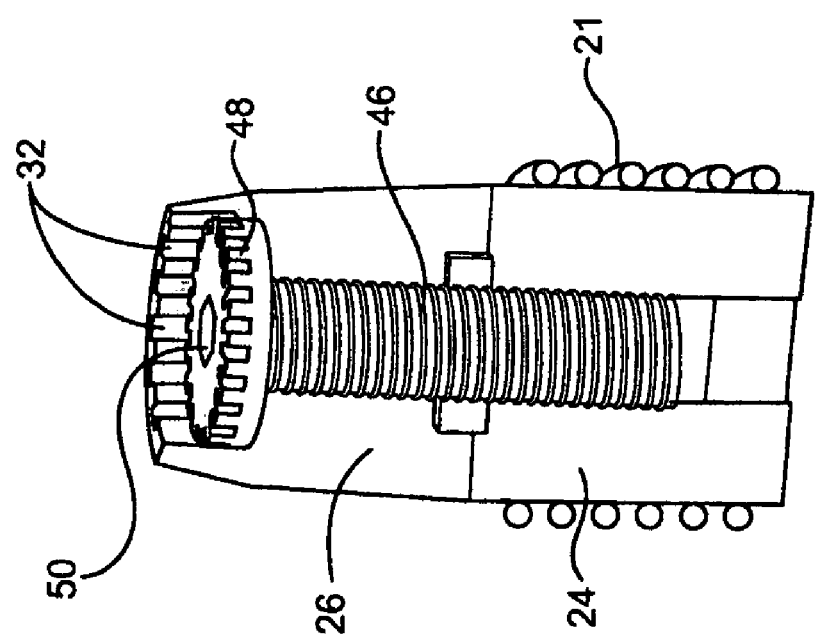
FIG. 3 Shows the dental implant, the abutment and the screw which attaches the abutment to the dental implant in a screwed down tightened position. The dental implant and the abutment are shown in cross section, the cross section being lateral (sagittal) in direction.

FIG. 4 shows yet another view of the implant and the abutment with the screw in a tightened position holding the assembly together. This view shows clearly the grooves on the top of the screw and the top of the abutment which allows for the locking fill material. The dental implant body and the abutment are shown in cross section, the cross section being lateral (sagittal).

Figure 5:
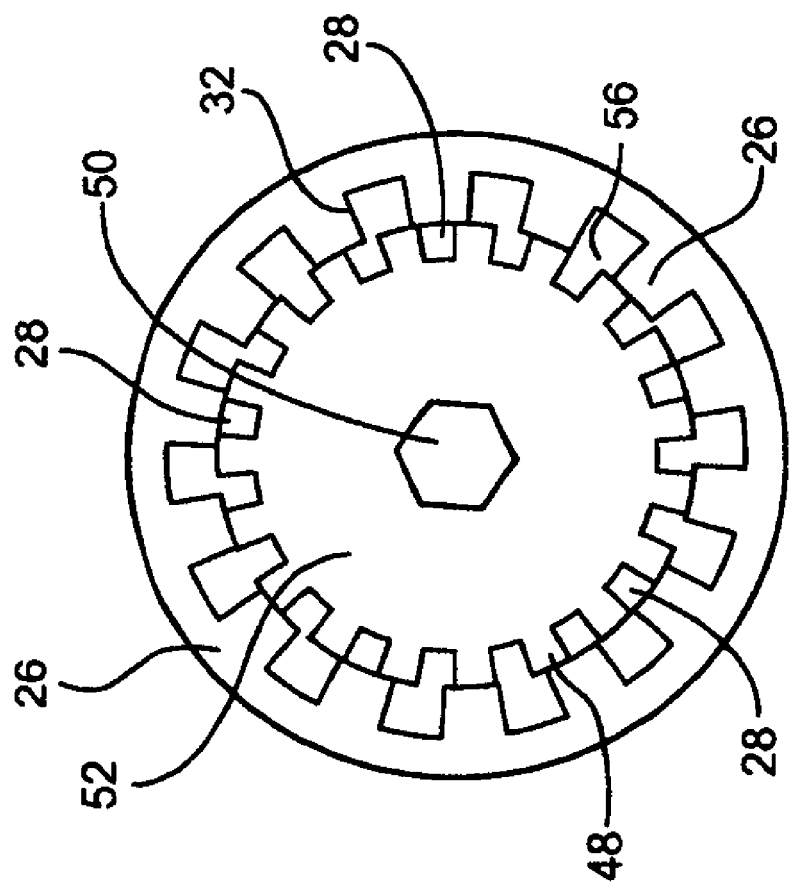

FIG. 5 Shows a direct overhead view of the screw head and the top of the abutment. This view also clearly shows the voids of both the head of the screw and the abutment which provide the opportunity to lock the head of the screw in place to the abutment when filled with a filling material. This, then, allows for one integrated unit of the screw, the implant body and the abutment.

Figure 6:
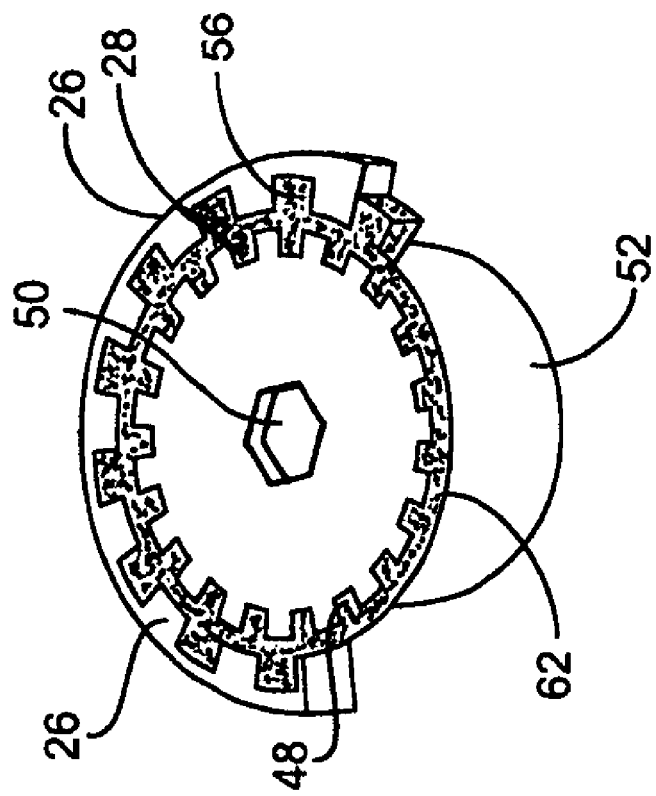

FIG. 6 Shows the head of the screw and a sagittal section of the abutment. Also shown are filled void areas located on the lateral areas of the screw head, the medial areas of the abutment and the septic seal ring filled void area of the proximal ends of both the screw head and the abutment. These void areas are shown as filled as they would be in the final locking state. It is to be noted, the seal ring does not extend to the distal end of the screw head nor to the distal end of the voids in both the screw head and the abutment; thus, assuring metal to metal contacts distal to the septic seal ring. Not shown is any portion of the body of the screw and the screw threads nor the sealed area where the abutment meets the implant body.

FIG. 7 Is a depiction of what the polymerized locking material would look like as though all the metal solid material had been dissolved around it as it were to be observed from the outside looking toward the center of the screw.

FIG. 8 Is a depiction of what the polymerized locking material would look like as though all the metal, solid material had been dissolved around it as it were to be observed from the inside looking toward the outer circumference of the abutment.

FIG. 9 The same as FIGS. 7 and 8 but from an overhead, top view.

DRAWING REFERENCE NUMERALS

20 Prosthetic crown
22 Bone supporting implant body
24 Implant body
26 Abutment
28 Voids in screw head
30 Marginal edge of prosthetic crown
32 Voids in abutment
34 Hex void area of abutment
36 Hex area of implant body, fits into 34
38 Screw threads in bore-hole of implant body
39 Septic void area at distal end of threaded bore-hole
40 Implant body, same as 24
44 Distal external end of abutment
46 Screw with threads
48 Voids lateral side of screw head
50 Hex wrench void top of screw
51 Shoulder screw seat of abutment
52 Screw head
54 Typical metal to metal contact of screw head to abutment metal protrusion
56 Void of screw head and void of abutment in approximation
58 Locates proximal end of implant abutment assembly
60 Distal end of assembly
62 Septic seal area of proximal ends of screw head and the abutment
64 Lower compression edge of locking material of abutment fill area
66 Lower tension edge of locking material of abutment fill area
68 Top of abutment locking material
70 Top of screw locking material
72 Side wall of locking material of abutment
74 Locking material wall facing center of screw
76 Lower compression edge of locking material of screw fill area

DETAILED DESCRIPTION—PREFERRED EMBODIMENTS

When the head of 52; FIG. 5 is tightened to a given manufacturer's specifications, usually addressed in, Newton centimeters of torque, abutment 26, FIG. 2 becomes joined to implant body 24 as a result of screw 46 being threaded into the bore hole 38 of implant body. Abutment 26 achieves stability from spinning in a rotating manner about the implant body by fitting the hex voided area 34 of abutment 26 over the hex raised area 36 of the implant body 24. (Observed from side view only). FIG. 5; Once the abutment is screwed and secured into place the approximating voided areas of the screw head 48 and the abutment 32 are then filled with a plasticized material such as composite dental filling material, dental amalgam or dental cement or any compatible, similar material. Once the material sets up and is hardened it locks the screw head 52 into its relationship with the abutment 26 just to the lateral area of the screw head. The design of the voided areas on the screw head and that of the voided areas of the abutment are such that in any given position there are some approximating void areas such as 56. In any given position there are also some areas of metal to metal contact 54 of the most lateral walls of the screw head and most immediate internal walls of the abutment to provide lateral stability of the head of the screw in its relationship to the abutment internal walls. Approximating voided areas may be partial or complete and said metal to metal contact areas may be partial or complete. In any possible final desired position there will be some approximating voided areas 56 and some metal to metal 54 areas.

The shapes of the voided areas on the screw head and the abutment can be of any infinite number of geometric configurations including etched areas. Voided areas can be spaced or sequenced so that they can be of any multiplicity of configurations of progressions, digressions or symmetries. Voided areas on either the abutment or the screw head can be larger or smaller in relation to each other or the same size or any variation thereof. Voided areas may have projections within them to effect retention of the fill material. The only real criteria of the size, shape and sequence of the voided areas is that in any final position of the screw head to the abutment some of the voided areas of the screw head and the abutment approximate each other either partially or completely. FIG. 5; Metal to metal contact areas 54; of the screw head and the abutment must also result from the size shape and sequence of the metal projections. Metal projections are those areas that are not void areas. Voided areas 48 in the screw head 52 and any approximating voids 32 of abutment 26, such as 56 are then filled with any plasticized material such as light cured filling material, chemical cured material, dual cure, two part chemical metal reactions such as dental amalgam or any material that can then harden and be placed in the voided spaces which will cause a locked relationship to any movement of the head of the screw to the abutment.

FIGS. 2, 3, 4, 5 & 6 Voided areas in the screw head and the abutment approximating voids can be of any configuration of size, shape, sequence and progression as in depth, width and height and projections out of any of those voids as long as the opportunity remains for the final position of the screw to allow for approximating voids to exist which can then be filled as stated above and allow for metal to metal contacts of the screw head and the approximate abutting area. Walls of the voids need not be flat, rectangular or of any prescribed configuration or sequence and could be etched areas.

Materials to fill in the voids to bring about the locked result can be of such a character that they can be dislodged with a device such as a dental ultrasonic cleaner or a drill. The effect of this is that should untoward circumstances arise relative to the dental implant once the fill material is removed in a satisfactory manner the screw can be removed and the abutment removed to achieve whatever goal is appropriate.

Manufacturers of dental implants need only allow for the presence of the voids in the screw head and the peripheral internal approximating area of the abutment. There are no additional parts that need to be manufactured. This can be done by their casting techniques, milling techniques, ablative techniques, welding techniques or any other technique or combination thereof. This is a great simplification over all other prior art. FIG. 5; Areas could be etched as well and could function as void areas, the only criteria being to have enough voided open space to allow the placement of fill material and to allow for the metal to metal contact areas. Said metal to metal contacts are made either partially or completely 54 in the relationship of the screw head 52 to the internal metal walls of the abutment 52 regardless of any final position of the screw head.

Septic Space

Figure 2:
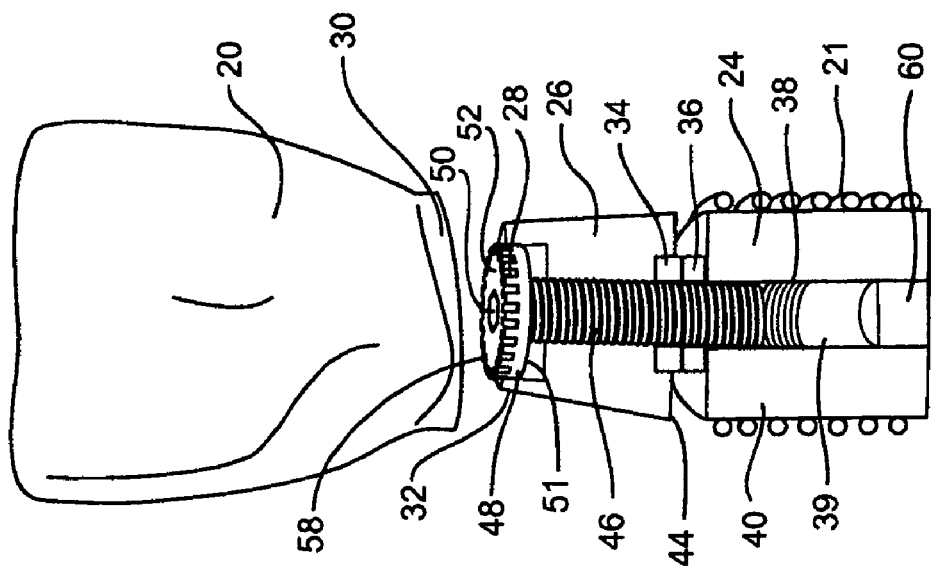
FIG. 2 Shows an exploded visualization of a prosthetic crown, the dental abutment, the implant body and the screw that holds the assembly together. The crown is attached to the abutment normally by cementation.
Figure 1:
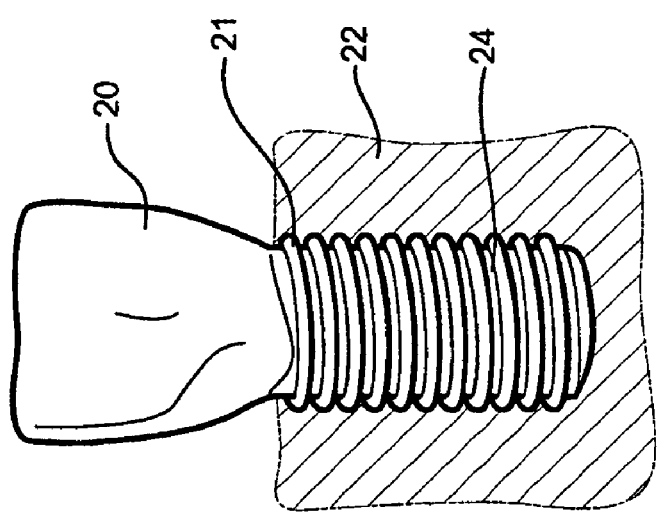
FIG. 1 Shows a prosthetic crown upon a dental implant imbedded in bone. Not seen is this view is the abutment that the prosthetic crown is cemented to since its visualization is obscured by the crown itself.

The septic space area is that space which exists between the periphery of the screw FIG. 2; 46 and the internal peripheral threaded wall of the abutment 26 as well as the periphery of the screw and the threaded wall 38 area of the implant body. Additional space occurs at the end of the screw space at the distal end of the implant body 39.

This septic space area is an ideal area for microbial organisms to grow. A sealing material is placed between the interface of the abutment and the implant body. The second seal to the area is then effected by either a top layer of the fill material on the screw head FIG. 2; 52 or a void is created around the periphery of the screw head FIG. 6; 62 and or a like area of the internal periphery of the approximating abutment area. A septic seal is accomplished by sealing a voided area, that is of any shape, around the entire circumference of the head of the screw and the internal approximating area of the abutment or both. These areas are then filled at the same time the other voided areas are filled to effect the screw head-lock. Or a layer of the fill material could be placed on top of the screw head to effect a similar result. This, then, provides an oral fluid seal of the proximal end of the assembly. As stated, the distal end of the septic area would be effected by placing a compatible seal substance such as dental cement between the interface of the abutment 26 and the implant body 24. The septic sealed area could no longer be an area of continuing microbial growth since it is sealed off from nutrient supplies, mouth micro organisms and salivary oral fluids.

FIGS. 7, 8 & 9 The fill material in these figures depicts how at the compression point angle of the abutment 64 and the compression point angle of the screw 76 force the solid fill material toward the distal end of the of the entire fill area by any unscrewing-rotational force effecting a true locking result. The fill material, as a result of the angled walls causing a narrower opening at the proximal end, causes any counter rotational effect upon the screw to compress the fill material in a distal direction.

The result of this is that the fill material under any counter rotational forces creates an even greater locking effect and prevents any likelihood of the fill material from being expressed in a proximal direction.

Ramifications:

This invention can be used in any place in industry or consumer devices where a screw head is desired to be locked to any properly prepared abutting area. Areas where a hermetic seal would wish to be accomplished at the head of the screw could benefit from this invention. Any circumstance where vibration, torque, heating or cooling might cause a screw head to loosen in its relationship to an abutting area would benefit from the head-lock invention. Areas where a screw is inside a closed sealed area would benefit from this invention.

Although the description above contains many specifications, these should not be construed as limiting the scope of the embodiment but as merely providing illustrations of some of the presently preferred embodiments. For example the voids and spacing of the voids in both the abutment area and the screw head area can be of any multiplicity of shapes and sequences as long as they allow for the final end position of the screw head to have approximating void areas in entirety or part and allow for areas of metal to metal contact in entirety or part.

Thus, the scope of the embodiment should be determined by the appended claims and their legal equivalents, rather than by the examples given.

The invention claimed is:

1. A locking system for screws used in securing an abutment to a dental implant comprising:
   a) an abutment, said abutment being positioned over an implant body having a bore hole formed therein, said abutment having an upper portion, said upper portion of said abutment having a plurality of spaced-apart grooves formed therein, and a space for receiving a screw head;
   b) a screw being threaded into said bore hole, said screw having a head, the head of said screw being fitted into the space for receiving a screw head in said abutment, said screw head also having a plurality of spaced-apart grooves formed therein, such that when said screw is tightened into said abutment, at least two of said plurality of spaced-apart grooves formed in said screw head are operatively aligned with at least two of said plurality of spaced-apart grooves formed in said abutment; and
   c) a quantity of fill material, placed in said abutment such that the plurality of spaced-apart grooves in said abutment and the plurality of spaced-apart grooves in said screw head are filled with said quantity of flowable fill material to create a solid bond between said screw head and said abutment, and further wherein said quantity of flowable fill material is selected from the group of composite dental filling material, dental amalgam and dental cement.

2. The locking system of claim 1 wherein the quantity of fill material also forms a seal in said abutment.

3. The locking system of claim 1 wherein each of the plurality of spaced-apart grooves formed in said abutment has a geometric shape.

4. The locking system of claim 3 wherein each of the plurality of spaced-apart grooves formed in said screw head has a geometric shape.

5. The locking system of claim 4 wherein when the at least two of said plurality of spaced-apart grooves of said abutment and said screw head are operatively aligned, the geometric shapes of said at least two of said plurality of spaced-apart grooves in said abutment and said screw head need not be in perfect alignment.

6. A method of installing a dental implant comprising the steps of:
   a) drilling a hole in a patient's jawbone;
   b) securing an implant body into said patient's jawbone;
   c) placing an abutment, over said implant body, said abutment having an upper portion, said upper portion of said abutment having a plurality of spaced-apart grooves formed therein, and a space for receiving a screw head;
   d) threading a screw into said implant body, said screw having a head, the head of said screw being fitted into the space for receiving a screw head in said abutment, said screw head also having a plurality of spaced-apart grooves formed therein, such that when said screw is tightened into said abutment, at least two of said plurality of spaced-apart grooves formed in said screw head are operatively aligned with at least two of said plurality of spaced-apart grooves formed in said top of said abutment;
   e) placing a quantity of fill material in said abutment such that the plurality of spaced-apart grooves in said abutment and the plurality of spaced-apart grooves in said screw head are filled with said quantity of fill material; and
   f) curing said quantity of fill material to create a solid bond between said screw head and said abutment.

7. The method of claim 6 wherein the quantity of fill material also forms a seal in said abutment.

8. The method of claim 7 further comprising the step of forming a second seal within said abutment.

9. The method of claim 8 wherein the second seal comprises a top layer of the fill material on the screw head.

10. The method of claim 9 wherein said second seal further comprises a seal formed to fill a voided area formed between the screw head and the abutment.

11. The method of claim 9 wherein said second seal comprises a seal formed by said quantity of fill material completely filling the space for receiving a screw head in said abutment.

12. The method of claim 9 wherein second seal comprises a seal formed by said quantity of fill material completely filling the space between the implant body and said abutment.

13. The method of claim 6 wherein the quantity of fill material is selected from the group of composite filling material, amalgam and dental cement.

14. The method of claim 6 wherein each of the plurality of spaced-apart grooves formed in said top of said abutment has a geometric shape.

15. The method of claim 14 wherein each of said plurality of spaced-apart grooves formed in said screw head has a geometric shape.

16. The method of claim 15 wherein when the at least two of said plurality of spaced-apart grooves of said abutment and said screw head are operatively aligned, the geometric shapes of said at least two of said plurality of spaced-apart grooves in said abutment and said screw head need not be in perfect alignment.

* * * * *